United States Patent [19]

Duck et al.

[11] Patent Number: 4,876,187
[45] Date of Patent: Oct. 24, 1989

[54] NUCLEIC ACID COMPOSITIONS WITH SCISSILE LINKAGE USEFUL FOR DETECTING NUCLEIC ACID SEQUENCES

[75] Inventors: Peter Duck; Robert Bender, both of Ottawa; William Crosby, Saskatoon; John G. Robertson, L'Ange Gardien, all of Canada

[73] Assignee: Meiogenics, Inc., Columbia, Md.

[21] Appl. No.: 805,279

[22] Filed: Dec. 5, 1985

[51] Int. Cl.$^4$ ............... C12Q 1/68; C12P 19/34; C07H 19/06; G01N 33/566
[52] U.S. Cl. ........................... 435/6; 435/91; 436/501; 536/26; 536/27; 536/28; 935/77; 935/78
[58] Field of Search ............... 435/6, 91; 436/501; 935/77, 78; 536/26, 27, 28

[56] References Cited

U.S. PATENT DOCUMENTS

| | | | |
|---|---|---|---|
| 4,261,968 | 4/1981 | Ullman et al. | 436/546 |
| 4,359,535 | 11/1982 | Pieczenik | 435/5 X |
| 4,563,417 | 1/1986 | Albarella et al. | 435/7 X |
| 4,568,649 | 2/1986 | Bertoglio-Matte | 436/534 |
| 4,683,194 | 7/1987 | Saiki et al. | 435/91 X |

FOREIGN PATENT DOCUMENTS

| | | | |
|---|---|---|---|
| 0142299 | 5/1985 | European Pat. Off. | 435/6 |
| 2078370 | 1/1982 | United Kingdom | 435/7 |

OTHER PUBLICATIONS

Melton, D. et al., Nucleic Acid Research. 12: 7035–7056 (1984).

*Primary Examiner*—Robert J. Warden
*Assistant Examiner*—Jack Spiegel
*Attorney, Agent, or Firm*—John P. White

[57] ABSTRACT

A synthetic, non-naturally occurring molecule having the structure:

$$[NA_1-S-NA_2]_n$$

wherein $NA_1$ and $NA_2$ are noncomplementary nucleic acid sequences;
wherein —S— is a scissile linkage; and
wherein n is an integer from 1 to 4.

Variations of this molecule and methods for using the molecules for detecting nucleic acid sequences are provided.

53 Claims, 2 Drawing Sheets

= DNA TARGET SEQUENCE

▭ = DNA PROBE SEQUENCE

▦ = DNA NONTARGET SEQUENCE

NUCLEIC ACID COMPOSITIONS WITH SCISSILE LINKAGE USEFUL FOR DETECTING NUCLEIC ACID SEQUENCES

BACKGROUND OF THE INVENTION

Current DNA probe methodology basically involves attaching target DNA to a nitrocellulose filter by bringing it into contact with the filter directly or via the Southern transfer technique from an agarose gel. The DNA is then denatured and the filters baked to ensure firm attachment. Generally, the preparation of the DNA and the running of the gels is a time consuming, costly process requiring a reasonably high technical skill level.

The next step is to prepare the probe DNA. Probe DNA is prepared by labelling radioactively specific DNA by nick translation, polynucleotide kinase, or some other polymerase type copy reaction using nucleotides labelled with $^{32}P$. Once prepared, the probe DNA is permitted to hybridize with the bound target DNA. Hybridization is allowed to proceed at a suitable temperature, typically for several hours. The DNA probe will associate to form hybrid duplexes with any of the bound target DNA that has complementary base sequences. Extraneous material, including unbound probe DNA, is then washed away from the filter and the filter is then exposed to film sensitive to the radioactive label.

International Patent Application No. WO 84/03520 (Malcolm et al.) discloses a method of detecting nucleic acid sequences which utilizes tandem hybridization of a nucleic acid probe and an enzyme containing marker.

The method involves contacting the probe with a sample containing a complementary target sequence under hybridizing conditions. Before or after hybridization with the target sequence, the probe is attached by hybridization to an enzyme labelled marker polynucleotide which has a sequence complementary to a sequence on the probe.

U.S. Pat. No. 4,358,535 (Falkow et al.) discloses radioactively labeled nucleotide probes which are complementary to a target nucleic acid sequence of interest and a method of using these probes to detect the presence of a pathogen from which the target nucleic acid sequence is derived. The method comprises first fixing the target nucleic acid sequence to an inert support before hybridization with the probe. Next, the fixed nucleic acid is contacted with the radioactively labeled probe under hybridizing conditions, with hybridization taking place on the solid support. Then, the presence of the target nucleic acid sequence is determined by detecting the presence of any label on the inert support. A disadvantage of such a system is that the probe itself cannot be immobilized. If the probe of Falkow et al. is immobilized, rather than the target nuclei acid sequence, then the label molecules of the immobilized probe will be bound to the solid support regardless of whether the probe has hybridized with a target nucleic acid sequence. The result would not permit the detection of the presence of target nucleic acid.

European Patent Application Publication No. 0 117 440 discloses non-radioactive chemically labeled polynucleotide probes and methods of using the probes. The methods disclosed are similar to the method of Falkow et al. in that the target nucleic acid sequence is fixed to a solid support before hybridization.

Recently, other detection systems have been developed, such as fluorescent tags or color change enzyme systems. However, such systems have had significant problems with sensitivity and background levels (noise).

U.S. Pat. No. 4,362,867 (Paddock) discloses a hybrid nucleic acid construction which comprises two complementary deoxynucleotide sequences which are hybridized to form a double-stranded helical structure. Situated between and covalently bonded to the two deoxynucleotides is a ribonucleotide sequence. The construction forms a single unit, in which none of the nucleotide sequences repeat themselves.

The present invention provides a method for the detection of specific DNA or RNA sequences in a test (target) DNA solution. The method provides a means of specifically cleaving the nucleic acid sequence of the probe in at least one point so as to remove any detectable reporter molecules not bound to a complementary target DNA sequence and thereby improve the signal to noise ratio of the detection system. Such a system enables the use of very high probe concentrations to drive the hybridization reaction without a corresponding increase in background noise level.

SUMMARY OF THE INVENTION

The present invention concerns a synthetic, non-naturally occurring molecule having the structure:

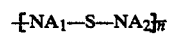

wherein $NA_1$ and $NA_2$ are noncomplementary nucleic acid sequences;
wherein —S— is a scissile linkage; and
wherein n is an integer from 1 to 1,000.
A synthetic, non-naturally occurring molecule is provided which has the structure:

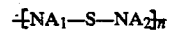

wherein $NA_1$ and $NA_2$ are nucleic acid sequences;
wherein —S— is a scissile linkage; and
wherein n is an integer from 2 to 1,000.
A molecule is provided which has the structure:

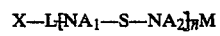

wherein $NA_1$ and $NA_2$ are nucleic acid sequences;
wherein —S— is a scissile linkage;
wherein n is an integer from 1 to 1,000;
wherein the solid lines represent chemical bonds;
wherein X is a solid support;
wherein L is a chemical entity which links $NA_1$ to the solid support; and
wherein M is a marker.
The present invention also pertains to a molecule having the structure:

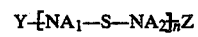

wherein $NA_1$ and $NA_2$ are nucleic acid sequences;
wherein —S— is a scissile linkage;
wherein n is an integer from 1 to 1,000;
wherein Y is absent or is a chemical entity which confers a unique identifying characteristic; and
wherein Z is absent or is a chemical entity which confers a different unique identifying characteristic.

A method of detecting in a sample the presence of a nucleic acid sequence of interest comprises:
- (a) contacting the sample with a non-immobilized molecule of the present invention, which comprises a nucleic acid sequence having a detectable marker attached and which is substantially complementary to the nucleic acid sequence of interest, under hybridizing conditions;
- (b) immobilizing the resulting molecule on a solid support;
- (c) treating the immobilized molecule so as to cleave the scissile linkage;
- (d) separately recovering the immobilized molecule; and
- (e) detecting the presence of the marker on the immobilized molecule and thereby the nucleic acid sequence of interest.

Another method of detecting in a sample the presence of a nucleic acid sequence of interest comprises:
- (a) contacting the sample with an immobilized molecule of the present invention which comprises a nucleic acid sequence having a detectable marker attached and which is substantially complementary to the nucleic acid sequence of interest, under hybridizing conditions;
- (b) treating the immobilized molecule so as to cleave the scissile linkage;
- (c) separately recovering the immobilized molecule; and
- (d) detecting the presence of the marker on the immobilized molecule and thereby the nucleic acid sequence of interest.

DETAILED DESCRIPTION OF THE INVENTION

Figure 1:
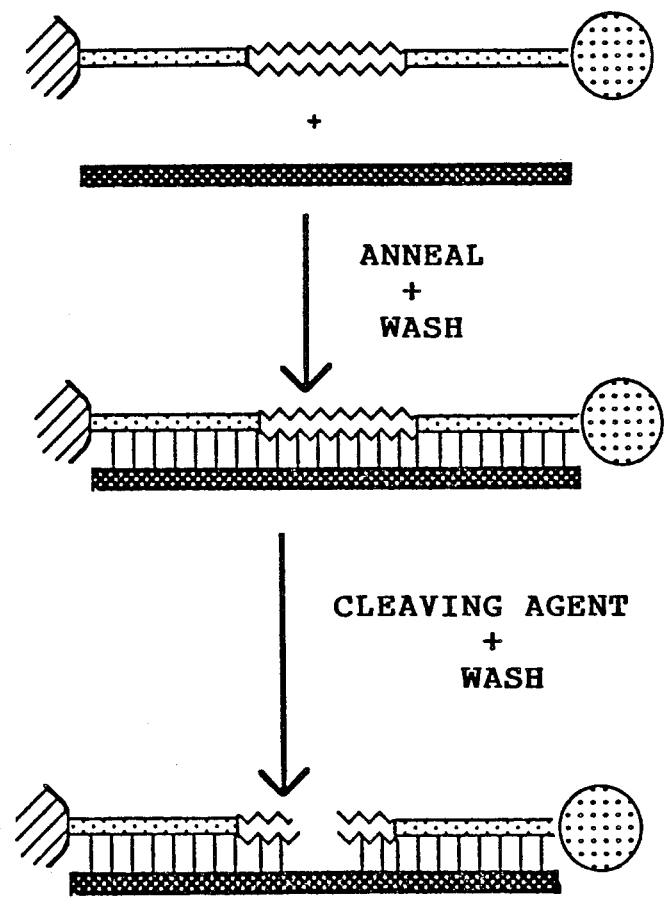
FIG. 1 depicts the nucleic acid probe of the present invention and the different results obtained when this probe is contacted with a complementary target DNA sequence (left side of FIGURE) and a non-complementary non-target DNA sequence (right side of FIGURE).
Figure 1:
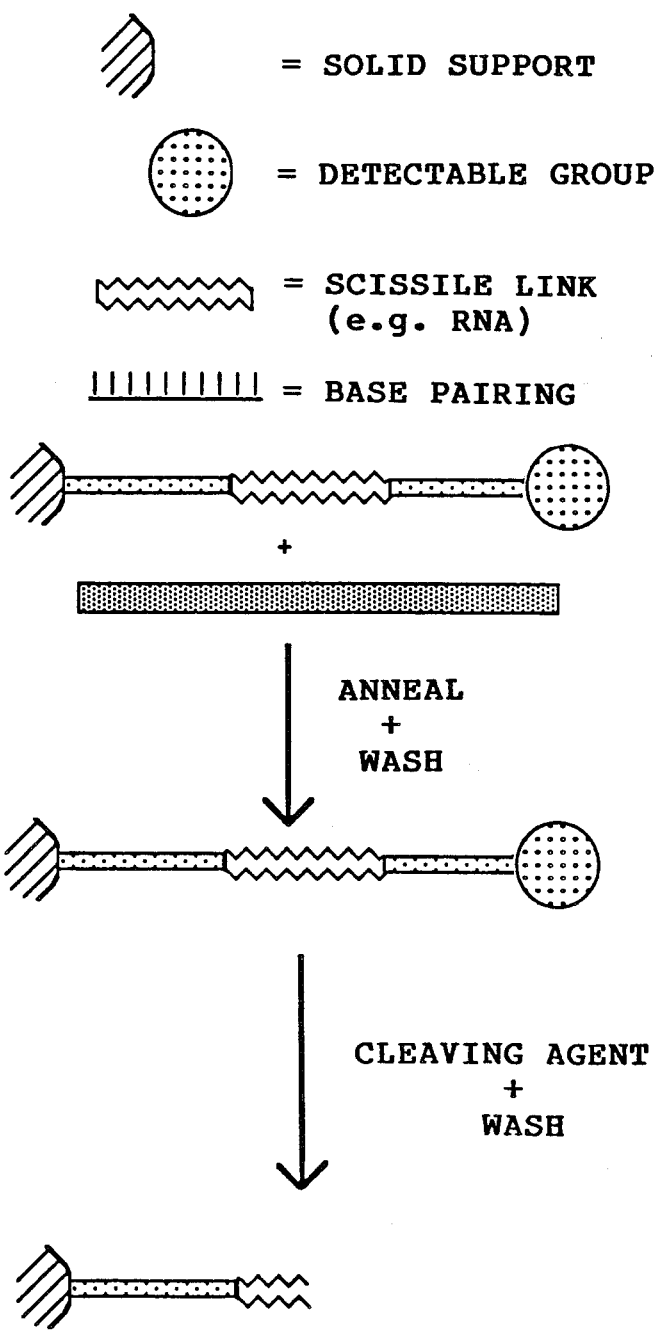

The present invention concerns a synthetic, non-naturally occurring molecule having the structure:

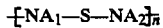

wherein $NA_1$ and $NA_2$ are noncomplementary nucleic acid sequences;
wherein —S— is a scissile linkage; and
wherein n is an integer from 1 to 1,000.

A synthetic, non-naturally occurring molecule, is provided, which has the structure:

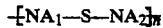

wherein $NA_1$ and $NA_2$ are nucleic acid sequences;
wherein —S— is a scissile linkage; and
wherein n is an integer from 2 to 1,000.

In the molecules of the present invention, the dashed lines of the scissile linkage represent chemical bonds, which may be covalent bonds or hydrogen bonds.

Within molecules of the present invention $NA_1$ and $NA_2$ may be DNA sequences, which may or may not be the same sequence. Alternatively, the molecules may be constructed of RNA sequences, which may or may not be the same sequence, or $NA_1$ and $NA_2$ may be a combination of RNA and DNA sequences. The DNA or RNA sequences utilized may be naturally occurring sequences or they may be synthetically formed. Each of $NA_1$ and $NA_2$ may be from about 8 bases to 10,000 bases in length. Less than eight bases results in inefficient hybridization. Preferably, the sequences are about 5000 bases in length.

The molecules of the present invention may have detectable marker attached to one or more of the nucleic acid sequences, $NA_1$ or $NA_2$. This marker is contemplated to be any molecule or reagent which is capable of being detected. Examples of such detectable molecules are radioisotopes, radiolabelled molecules, fluorescent molecules, fluorescent antibodies, enzymes, or chemiluminescent catalysts. Another suitable marker is a ligand capable of binding to specific proteins which have been tagged with an enzyme, fluorescent molecule or other detectable molecule. One example of a suitable ligand is biotin, which will bind to avidin or streptavidin. Another suitable ligand is a hemin molecule, which will bind to the apoenzyme portion of catalase.

The present invention also concerns a composition comprising a solid support and a molecule of the present invention immobilized thereon. The immobilized molecule may have attached a detectable marker.

The molecules of the present invention have a scissile linkage which is capable of being cleaved or disrupted without cleaving or disrupting any nucleic acid sequence of the molecule itself or of the target nucleic acid sequence. As used herein, a scissile linkage is any connecting chemical structure which joins two nucleic acid sequences and which is capable of being selectively cleaved without cleavage of the nucleic acid sequences to which it is joined. The scissile linkage may be a single bond or a multiple unit sequence. An example of such a chemical structure is an RNA sequence. Other chemical structures suitable as a scissile linkage are a DNA sequence, an amino acid sequence, an abasic nucleotide sequence or an abasic nucleotide, or any carbohydrate polymer, i.e. cellulose or starch. When the scissile linkage is a nucleic acid sequence, it differs from the nucleic acid sequences of $NA_1$ and $NA_2$.

In molecules of the present invention in which n is greater than one, the unit $NA_1$—S—$NA_2$ repeats. It is contemplated that the unit may be the same within each repeat or it may vary randomly of in a defined pattern. The unit may vary in that $NA_1$ or $NA_2$ or both may vary within each repeat. $NA_1$ or $NA_2$ may vary in that they have different nucleic acid sequences from one repeat unit to the next. This variation may occur randomly such that in every repeat unit $NA_1$ and $NA_2$ are different. The variation also may occur in a defined pattern such that the variation repeats itself in every defined multiple of a unit. $NA_1$ and $NA_2$ may also vary in that the number of bases of each may vary, either greater or less, from one repeat to the next. This variation may also occur randomly or in a pattern. An example of a random variation where n=3 and both $NA_1$ and $NA_2$ vary is:

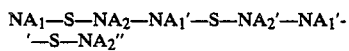

An example of a patterned variation where n=4 and both $NA_1$ and $NA_2$ vary is:

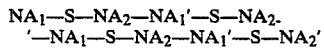

In both of the above examples, the solid lines joining each unit are chemical bonds which may be either hydrogen bonds or covalent bonds.

The repeat unit may also vary by variations in the scissile linkage such that one unit has a scissile linkage which is an amino acid sequence and another unit has a scissile linkage which is an RNA sequence. The variatiion in the scissile linkage may also be in a random or patterned fashion as discussed above. Also, the repeat units may vary by any combination of the above-mentioned differences in $NA_1$, $NA_2$ or the scissile linkage and the variations may be random or patterned.

A molecule is provided which has the structure:

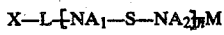

wherein $NA_1$ and $NA_2$ are nucleic acid sequences;
wherein —S— is a scissile linkage;
wherein n is an integer from 1 to 1,000;
wherein the solid lines represent chemical bonds;
wherein X is a solid support;
wherein L is a chemical entity which links $NA_1$ to the solid support; and
wherein M is a marker.

In the molecule represented above, X may be a silicaceous, cellulosic, or plastic material or controlled pore glass. The chemical bonds represented by solid lines may be either covalent or hydrogen bonds. The dashed lines of the scissile linkage also represent chemical bonds, which may be covalent or hydrogen bonds. M is a detectable marker which may be a radioisotope, a radiolabeled molecule, a fluorescent molecule or a suitable ligand. M may also comprise a marked nucleic acid sequence complementary to a sequence within $NA_2$. L may comprise a nucleic acid which has a sequence substantially complementary to the sequence of $NA_1$, wherein L is chemically bound to the solid support and wherein L links $NA_1$ to the solid support by means of hydrogen bonds between complementary nucleic acid sequences.

The present invention also concerns a molecule having the structure:

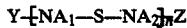

wherein $NA_1$ and $NA_2$ are nucleic acid sequences;
wherein —S— is a scissile linkage;
wherein n is an integer from 1 to 1,000;
wherein Y is absent or is a chemical entity which confers a unique identifying characteristic; and
wherein Z is absent or is a chemical entity which confers a different unique identifying characteristic.

This embodiment of the invention, which has Y and Z conferring unique identifying characteristics to the molecule, is suitable for use in a biphasic concentration system. In such a molecule, when the identifying characteristic of Y is hydrophobicity or hydrophilicity, the identifying characteristic of Z is hydrophilicity or hydrophobicity, respectively. Also, one of Y or Z may be absent in which case the other is a hydrophobic entity. In this case, the nucleic acid sequence, $NA_1$ or $NA_2$, which does not have Y or Z attached will serve as the hydrophilic portion of the molecule. Also, the Y or Z group may be an identifying marker and the other group a hydrophobic group. Also, Y or Z may serve as a linker entity which attaches the molecule to a solid support.

In the molecule represented above, the chemical bonds represented by solid lines may be either covalent or hydrogen bonds. The dashed lines of the scissile linkage also represent chemical bonds, which may be either covalent or hydrogen bonds. This molecule may have a detectable marker attached to one of $NA_1$ or $NA_2$.

The molecules of the present invention are useful for detecting target DNA which is bacterial DNA, i.e. *Salmonella* and *Escherichia coli*, or viral DNA, i.e. herpes simplex virus types I and II, adenovirus, and cytomegalovirus. Detection of bacterial or viral DNA is useful for diagnosing human, plant, or animal diseases. One particular use is the detection of human infectious disease, such as gonorrhea. Another use is in the diagnosis of human genetic disorders, i.e. sickle cell anemia.

The molecules of the present invention are useful as probes for detecting nucleic acid sequences and may be utilized in two different forms: (1) immobilized to a solid support for use in a heterogeneous system; or (2) non-immobilized for use in a homogeneous system. In the immobilized form, the nucleic acid sequence having a free terminus has a detectable marker attached. Examples of suitable solid supports for immobilizing the probe are those which are silicaceous materials, cellulosic materials, plastic materials, i.e. polystyrene, or controlled pore glass (CPG). The preferred solid support is any solid which has reactive groups, such as hydroxyl, carboxyl, or amino groups, which are capable of attaching to the molecules of the present invention. Also, the molecules of the present invention may be attached to a solid support by adhesion to the support. In the non-immobilized form, the terminus that does not have the marker attached may have a nucleic acid sequence attached to its free end that is complementary to a previously immobilized sequence.

The immobilized molecules of the present invention may be attached to a solid support directly via reaction of the 3′ end of the molecule with the support, or indirectly via a chemical entity L which links the molecule to the support by reacting with the 3′ end of the molecule to form a covalent bond and reacting with the solid support to form another covalent bond. Another version of the linking entity is one which as a first reactive site which is a nucleic acid sequence complementary to a sequence at the 3′ end of the molecule of the present invention which is capable of forming hydrogen bonds with the molecule and a second reactive site which is capable of forming a covalent or hydrogen bond with the solid support. The present invention also contemplates attachment of the novel molecules to a solid support by diazo coupling.

Suitable chemical linking entities are any reactive nucleic acid-binding ligand capable of attaching the molecule of the present invention to a solid support without impairing the molecule's nucleic acid function. Examples of such linking entities are listed in European Patent Application Publication No. 0 130 523 and may be selected from any derivative of the following classes of nucleic acid intercalator compounds: acridine dyes, phenanthridines, phenazines, phenothiazines, quinolines, aflatoxins, polycyclic hydrocarbons and their oxirane derivatives, actinomycins, anthracyclinones, thiaxanthenones, anthramycin, mitomycin, platinum complexes, fluorenes, fluorenones and furocoumarins.

A method of detecting in a sample the presence of a nucleic acid sequence of interest comprises:

(a) contacting the sample with a non-immobilized molecule of the present invention which comprises a nucleic acid sequence having a detectable marker attached and which is substantially complementary to the nucleic acid sequence of interest, under hybridizing conditions;

(b) immobilizing the resulting molecule on a solid support;

(c) treating the immobilized molecule so as to cleave the scissile linkage;

(d) separately recovering the immobilized molecule; and (e) detecting the presence of the marker on the immobilized molecule and thereby the nucleic acid sequence of interest.

Another method of detecting in a sample a nucleic acid sequence of interest comprises:

(a) contacting the sample with an immobilized molecule of the present invention which comprises a nucleic acid sequence having a detectable marker attached and which is substantially complementary to the nucleic acid sequence of interest, under hybridizing conditions;

(b) treating the immobilized molecule so as to cleave the scissile linkage;

(c) separately recovering the immobilized molecule; and (d) detecting the presence of the marker on the immobilized molecule and thereby the nucleic acid sequence of interest.

Another method of detecting in a sample a nucleic acid sequence of interest comprises:

(a) contacting, under hybridizing conditions, the sample with an aqueous solution comprising a molecule represented by the structure $Y \vdash NA_1 - S - NA_2 \vdash_n Z$ which comprises a nucleic acid sequence having a detectable marker attached and which is substantially complementary to the nucleic acid sequence of interest and which includes a hydrophobic entity Y and a hydrophilic entity Z;

(b) mixing the resulting solution with a nonpolar solvent to form a biphasic solution in which the molecule is present at the phase interface of the biphasic solution, with Y being oriented in one phase and Z being oriented in the other phase;

(c) treating the molecule so as to cleave the scissile linkage;

(d) recovering the molecule so treated; and (e) detecting the presence of the marker and thereby detecting the nucleic acid sequence of interest.

A further method of detecting in a sample a nucleic acid sequence of interest comprises:

(a) contacting, under hybridizing conditions, the sample with a non-immobilized molecule of the present invention which comprises a nucleic acid sequence having a detectable marker attached and which is substantially complementary to the nucleic acid sequence of interest so as to form a hybridized product;

(b) contacting, under hybridizing conditions, the product of step (a) with a nucleic acid sequence which is complementary to the sequence of the non-immobilized molecule of step (a) but has about 1-10 fewer bases and is capable of rendering the molecule undetectable when hybridized to the molecule, so that the nucleic acid sequence complementary to the molecule hybridizes with unhybridized molecule; and (c) detecting the presence of the marker, thereby the presence of the hybridized product, and thereby the nucleic acid sequence of interest.

The present invention provides a method for detecting the presence of a foreign pathogen in a sample qualitatively which comprises detecting a nucleic acid sequence characteristic of the pathogen using any of the methods of the present invention. It also provides a quantitative method for measuring the amount of a foreign pathogen in a sample which comprises detecting a nucleic acid sequence characteristic of the pathogen using any of the methods of the present invention.

A method for quantitatively determining in a sample the amount of a nucleic acid sequence of interest comprises:

(a) contacting the sample with a predetermined amount of a non-immobilized molecule of the present invention which comprises a nucleic acid sequence having a detectable marker attached and which is substantially complementary to the nucleic acid sequence of interest, under hybridizing conditions;

(b) immobilizing the resulting molecule on a solid support;

(c) treating the immobilized molecule so as to cleave the scissile linkage;

(d) separately recovering the immobilized molecule; and (e) quantitatively determining the amount of marker present on the immobilized molecule and thereby the amount of nucleic acid sequence of interest.

Another method for quantitatively determining in a sample the amount of a nucleic acid sequence of interest comprises:

(a) contacting the sample with a predetermined amount of an immobilized molecule of the present invention which comprises a nucleic acid sequence having a detectable marker attached and which is substantially complementary to the nucleic acid sequence of interest, under hybridizing conditions;

(b) treating the immobilized molecule so as to cleave the scissile linkage;

(c) separately recovering the immobilized molecule; and (d) quantitatively determining the amount of marker present on the immobilized molecule and thereby the amount of nucleic acid sequence of interest.

A further method for quantitatively determining in a sample the amount of a nucleic acid sequence of interest comprises:

(a) contacting under hybridizing conditions the sample with an aqueous solution comprising a molecule represented by the structure $Y \vdash NA_1 - S - NA_2 \vdash_n Z$ which comprises a nucleic acid sequence having a detectable marker attached and which is substantially complementary to the nucleic acid sequence of interest and which includes a hydrophobic entity Y and a hydrophilic entity Z;

(b) mixing the resulting solution with a nonpolar solvent to form a biphasic solution in which the molecule is present at the phase interface of the biphasic solution, with Y being oriented in one phase and Z being oriented in the other phase;

(c) treating the molecule so as to cleave the scissile linkage;

(d) recovering the molecule so treated; and (e) quantitatively determining the amount of marker and thereby the nucleic acid sequence of interest.

The molecules of the present invention are useful as probes for DNA or RNA. Before hybridization, the probe molecule may be immobilized on a suitable solid support. Such immobilization is typically effected by a bond between the support and one of the two DNA sequences of the molecule or simply by adhesion of the molecule to the solid support. The other DNA sequence included within the molecule contains a detectable marker. After hybridizing the DNA sequences of the molecule with a DNA sequence of interest, disrupting the linkage between the immobilized DNA sequence of the molecule and the DNA sequence of the molecule which contains the detectable marker, and removing any material not immobilized, e.g. by washing, the only detectable marker remaining is the detectable marker of hybridized molecules. Any non-hybridized sequences containing the detectable marker are no longer bound to the immobilized sequence, either by the linker or by hybridization and are therefore removed. Thus, the presence of the detectable marker indicates the presence of the sequence of interest.

Immobilizing the probe molecule prior to hybridization affords a high effective concentration of probe molecules for hybridization with the nucleotide sequence of interest. The effective probe concentration in this embodiment is significantly higher than that obtained by conventional methods in which the sequence of interest rather than the probe is immobilized prior to the hybridization step. After contacting the immobilized probe of this embodiment with material suspected of containing the sequence of interest, the probe molecules are contacted with an appropriate reagent, such as RNase if the scissile linkage is RNA, under suitable conditions to excise, cleave or digest the linkage or otherwise disrupt the linkage between DNA sequences of the probe. Unless the immobilized probe has hybridized with the sequence of interest, the RNA sequences are cleaved by the RNAse, and, unconnected to the sequence of interest, are removed by washing. Hence the presence, after washing, of the detectable marker indicates presence of the sequence of interest.

The molecules of the present invention may contain a homopolymer tail, e.g. poly dA, poly dT or any defined sequence complementary to a previously immobilized sequence. Before or after hybridization of the molecule to the nucleotide sequence of interest, the poly dA tail may be used to attach (via hybridization) the molecule to a previously immobilized poly dT fragment. Thus, the molecule may be hybridized to a sequence of interest in solution and may then be immobilized to eliminate unhybridized molecule prior to detection.

Another aspect of the present invention involves a biphasic concentration system. Such a system is useful for modifying the partition behavior of nucleic acid constructions. The biphasic system involves constructing a probe molecule with a scissile linkage and having a hydrophilic group at one end of the probe and a lipophilic group at the other end. Either of these groups may also serve as a detection molecule or an additional detection molecule can be attached to one end. If no hybridization to the sought after molecule takes place, then, in a biphasic solution, cleavage of the scissile linkage causes the dispersion of the hydrophilic and lipophilic groups to their respective solubility preference. However, if hybridization has occured, then the hydrophilic and lipophilic groups are bridged together and remain concentrated at the interface. This interface can then be isolated and exposed to the appropriate visualizer for the specific marker utilized.

With respect to the hydrophobic/hydrophilic scissile linkage probe system, the following construct is contemplated. A short nucleic acid probe is attached to a lipophilic molecule (which may or may not also serve as a marker molecule). The probe is sparingly soluble in aqueous conditions but highly soluble in non-polar solvents. Hybridization is carried out in aqueous conditions. Upon subsequent addition of a non-polar, nonmiscible phase, the unhybridized probe partitions into this phase whereas the hybridized probe concentrates at the interface due to the additional hybridized component of hydrophilic DNA. This construct, unlike other partitioning constructs of the present invention does not require a scissile linkage.

Such a biphasic concentration system is useful in isolating small quantities of a target nucleic acid from a sample having a large aqueous volume. The sample is subjected to the biphasic concentration system and target material is concentrated at the interface of the two phases. The interface has a relatively small volume compared to that of the two phases. Sepration of the interface from the system results in the target nucleic acid sequence being present in relatively high concentration in a small volume of interface.

The biphasic concentration system is also useful in isolating mRNA from a sample. A biphasic probe molecule with a poly dT tail may be used to hybridize with the mRNA and then the mRNA is isolated using the solvent partitioning method of the present invention. Such a system has advantages over a poly dT column, such as faster isolation time and no problems with extraneous material clogging the column.

The purpose of the present invention is to provide a method for the detection of specific DNA or RNA sequences in a sample. The method provides a means of specifically cleaving the DNA sequence of the probe in at least one point so as to remove any detectable marker molecules not bound to a complementary target DNA sequence and thereby improve the signal to noise ratio of the detection system.

The differential lability of DNA and RNA may be exploited in a heterogeneous system to achieve the purpose of the present invention when the scissile linkage is an RNA moiety. Consider FIG. 1, which depicts the different results obtained when the DNA probe of the present invention is contacted with a complementary DNA target sequence and a non-complementary DNA sequence. Complementary target DNA hybridizes with the DNA strands of the probe so as to connect the DNA strand attached to the solid support with the DNA strand having the detectable marker after the scissile linkage has been disrupted. In the case where the probe comes in contact with non-complementary DNA, the marker is cleaved from the probe when the scissile linkage is disrupted. The result of such an arrangement is that a marker remains attached to the probe only if the probe has hybridized with a complementary target DNA sequence. The cleaved markers of non-hybridized probes are eluted from the system. This rids the system of unreacted detection component which causes high background noise. The only detection system component remaining is that which is hybridized to a target DNA molecule. When the remaining components of the detection system are added only hybridized material reacts. This enables the use of very high probe concentrations to drive the hybridization reaction without a corresponding increase in background noise level.

When the scissile linkage is an RNA sequence, the linkage may be cleaved by an enzyme destructive to RNA. Various RNases may be used to cleave an RNA link. When RNase A is used, only single stranded RNA (i.e., unhybridized) is cut so that the detection component is removed from unhybridized probe molecules, but hybridized probe molecules remain intact. When RNase H is used, only RNA found in an RNA/DNA double-stranded hybrid is cleaved. This leaves a single stranded DNA gap in a hybridized probe molecule which is then available for rehybridization with another component of the detection system. This type of differential lability makes it possbile to use a variety of detection systems.

It is contemplated that the scissile linkage may also be formed by one or a series of abasic nucleotides. Any modified base which can be differentiated from deoxy (A,T,G,C) may serve as a substrate for the formation of a cleavable point in a DNA sequence. That is to say that the base portion of the deoxyribonucleoside or the ribonucleoside may be removed either before or after synthesis of the probe. The scissile linkage in the probe sequence may be synthesized by using abasic precursor molecules or by enzymatically removing the base after synthesis. An example of the latter is as follows: when deoxyuridine is used during synthesis as the linker entity, one may subsequently remove the uracil base from the deoxyuridine by treatment with the enzyme N-uracil DNA glycosylase. This creates an abasic link wherever there was a deoxyuridine. This link is cleavable by basic conditions or by treatment with one of a group of enzymes called Ap endonucleases which can cleave at any abasic site. It should be noted that uridine moieties in the probe sequence may be created either through direct synthesis or by chemical deamination of cytosine moieties. There are indications in the literature that this deamination may be accomplished by judicious treatment with sodium bisulphite. After deamination of cytosine, the resulting uridine moiety may be converted to an abasic link by the action of N-uracil DNA glycosylase. Subsequent cleavage is then effected by either basic conditions or the action of Ap endonucleases. This latter approach allows a scissile linkage to be formed in pre-existing DNA so that non-synthetic or natural DNA sequences may be used as probes in a scissile link system.

With respect to Ap endonuclease activity, the enzyme may be selected such that the end product of its activity is a terminal sugar moiety. This may provide a substrate for a subsequent detection reaction.

A contemplated detection system is a system which utilizes a marker component that is a subunit of a luminescent enzyme system, such as luciferase. Addition of the other subunit plus suitable cofactors and substrate results in luminescence which may then be amplified and detected.

Another contemplated detection system is a system having a solid probe matrix set up as a "dipstick" system having an enzyme attached to the probe. The probe matrix is dipped into a target DNA solution for a specified time at a specified temperature. It is then dipped in RNase to cleave off probe enzyme from probes which have not hybridized. Finally, after a brief washing the matrix is dipped in a solution of the enzyme's substrate which then allows a detectable reaction to occur (i.e., a color reaction).

The differential lability and scissile link cleavage tactics which are discussed above may be used in homogenous systems as well as heterogenous systems. The major problem with a homogeneous system, where the probe is not fixed to a solid support, is the prevention of the detection of unhybridized detection componentsso that background noise is not intolerable. This problem is overcome with the use of an agent that blocks the detectable marker from reacting. After hybridization has occurred, a competing nucleic acid counterprobe sequence may be added that bears an attachment that sterically hinders or blocks the participation of unhybridized marker in any further detection reaction. When the steric blocker is added before the addition of a secondary component required for the detection reaction, detection of unhybridized detection markers is blocked. When the blocker is introduced via an RNA complementary sequence, the procedure is reversible and the blocker may be effectively removed by adding an RNase.

The counter probe itself is constructed to be slightly shorter, i.e. about 1–5 base pairs, than the nucleic acids of the probe. This insures that the counterprobe is less efficient than target sequence at hybridizing with probe nucleic acid and therefore the counterprobe does not compete with the target sequence for the probe nucleic acid.

Probe molecules used for testing the scissile link concept have been constructed on a solid support medium (either silica gel or controlled pore glass) using either a hydrolysable linkage or a permanent (non-hydrolysable) linkage. Published chemical methods were used for this synthesis. (Alvarado-Urbina, G., G. M. Sathe, W. C. Liu, M. F. Gillan, P. D. Duck, R. Bender, and K. K. Ogilvie (1981), Automated Synthesis of Gene Fragments, Science 214: 270–274; Roberts, D. M., R. Crea, M. Malecha, G. Alvarado-Urbina, R. H. Chiarello, and D. M. Watterson (1985), Chemical Synthesis and Expression of a Calmodulin gene designed for a Site-Specific Mutagenesis, Biochemistry, in press; Van Boom, J. H., and C. T. Wreesman (1984), Chemical Synthesis of Small Oligoribonucleotides in Solution, In Oligonucleotide Synthesis—A Practical Approach, pp. 153–183, Ed. M. J. Gait, IRL Press). Standard protected deoxynucleoside monomers were obtained from commercial sources whereas protected deoxyuridine and the ribonucleoside monomers were prepared using published procedures. (Ti, G. S., B. L. Gaffney, and R. A. Jones (1982), Transient Protection: Efficient One Flask Synthesis of Protected Nucleosides, J. AM. Chem. Soc. 104: 1316). Synthesis was performed with a BIOLOGICALS automated synthesizer using a cycle time of 10 minutes for each DNA condensation and 12 minutes for each RNA condensation.

The following probe constructions were used in various test systems.

SCISSILE LINK PROBES

P. L.=Permanent Linkage to Solid Support
H. L.=Hydrolysable Linkage to Solid Support
1. MRC046:

2. MRC059:

5'd(TTTTTTTTTT)r(UUU-
U)d(TTTTTTTTTTTT)3'—H.L.

3. MRC060:

5'd(TTTTTTTTTTTT)R(UUU-
U)D(TTTTTTTTTT)3'—H.L.

4. MRC064:

5'd(TTTTTTTTTTTT)d(UUUUUUU-
U)d(TTTTTTTTTT)3'—H.L.

5. MRC068:

5'd(TTTTTTTTTTTTTTTT)d(UUUUUUU-
U)d(TTTTTTTTTT)3'—H.L.

6. MRC069:

5'd(GGGTAACGCCAG)r(GGUUUU)d(C-
CCAGTCAC)3'—H.L.

7. MRC070:

5'd(GGGTAACGCCAG)r(GGUUUU)d(C-
CCAGTCAC)3'—P.L.

8. MRC071:

5'd(TTTTTTTTTTTTTTTTT)r(U-
U)d(TTTTTTTTTT)3'—H.L.

Counter Probes

9. MRC043:

5'd(ACAACGTCGTGACTGGGA)3'—H.L.

10. MRC045:

5'd(ACAACGTCGTGACTGGGAA)3'—P.L.

11. MRC058:

5'd(ACAACGTCGTGACTGGGAAT)3'—P.L.

12. MRC062:

5'd(CAACGTCGTGACTG-
GGAAAACTTTTTTT)-3'—H.L.

13. MRC063:

5'd(CAACGTCGTGACTG-
GGAAAACTTTTTTT)-3'—P.L.

14. MRC067:

5'd(CAACGTCGTGACTG-
GGAAAACTTTTTTTTT)-3'—P.L.

15. MRC072:

5'd(GTTTTCCCAGTCAC-
GACGTTGTTTTTTTTTTTTT)-3'—P.L.

16. MRC073:

5'd(GTTTTCCCAGTCAC-
GACGTTGTTTTTTTTTTTTT)-3'—H.L.

EXAMPLE 1

Construction of Scissile Link Probes

Probe molecules 1–3 and 5–8 were shown to be cleavable at the ribonucleotides by a number of RNases including pancreatic RNase as well as by basic conditions (eg., 0.5M NaOH). Most general methods for cleavage by RNases and other routine procedures can be found in Maniatis et al. (Maniatis, T., E. F. Fritsch, and J. Sambrook, (1982), Molecular Cloning, A Laboratory Manual, Cold Spring Harbor Laboratory). Probe number 4 was treated with N-uracil glycosylase which removed the uracil base from the uridine moieties leaving an abasic linkage. Subsequent treatment with Ap endonuclease or mild base cleaved the linkage. For simplicity the detector molecule in the experiments was $P^{32}$, which was attached to the 5' end of the probe with polynucleotide kinase.

A scissile link probe (eg. MRC 068) was kinased with $P^{32}$ while the probe sequence was still attached to the solid support upon which it was synthesized. After cleavage with pancreatic RNase, the solid support was spun down in a Microfuge for a few seconds and the supernatant dried down and resuspended in a small volume for checking on a 20% polyacrylamide gel. The solid support remaining was found to have little or no radioactivity associated with it. All the radioactive counts were hydrolysed off by the RNase. When these counts were checked, electrophoretically, they were found to reside in the 14 base fragment 5' distally to the RNA link. Sometimes 1 or 2 ribonucleotides remained attached. When the remaining sequence was hydrolysed from the solid support with concentrated ammonium hydroxide and then kinased with $P^{32}$, it was found to correspond to the 3' distal DNA 10-mer. It may also have 1 or 2 ribonucleotides attached.

On the other hand, when the 5' labelled scissile link probe is hybridized to an excess of oligo dA (simulates an unknown) prior to treatment with pancreatic RNAse, little or no radioactive label is released from the solid support to which the probe is attached. The same is true when RNase H is used even though the RNA link is presumably cleaved. The oligo dA piece acts as a hybridization bridge between the 3' DNA 10-mer and the 5' DNA 14-mer, thereby preventing the release of the 5' $P^{32}$ labelled 14-mer into the supernatant. In this manner unhybridized probe material can be discriminated from hybridized probe material. Other experiments performed with MRC 070,5'-$P^{32}$ labelled probe which is homologous to a region of the single strand DNA phage M-13 yielded similar results. In these cases, M-13 is used as the unknown and is hybridized to the MRC-070 probe. After RNase treatment unhybridized probe is washed away from the solid support. The counts of radioactivity remaining associated with the solid support are a reflection of the amount of M-13 hybridized to the MRC 070 probe.

EXAMPLE 2

Construction of Counter Probes

Counter probe molecules 9 through 16 were used in experiments to determine suitable hybridization conditions. Sequences 9–14 have the same sequence as a short region of the single-stranded DNA phage M-13. Sequences 15–16 are complementary to this M-13 region. Initial experiments involved $P^{32}$ labelling a short synthetic sequence from M-13 (5" $P^{32}$-GTTTTCCCAGT- CACGACGTTG). Counterprobes complementary to this sequence and attached to a solid support were then used to remove the labelled sequence from solution. A variety of hybridization conditions were tried and the system was found to tolerate considerable variation. A factor which was found to considerably influence the efficiency of binding counterprobe to probe was the length of the non-specific arm between the solid support and the 3' end of the complementary sequence. In general, a 12-T arm pulled out virtually all of the labelled probe from solution within 30 minutes at an excess of about 4000X. With no T arm between the solid support and the complementary sequence, only about 60% of the labelled probe was removed from solution. An important point emerging from competition studies is that the counterprobe sequence complementary to the probe should be 1-5 bases shorter than the probe. Since the counterprobe is the same sequence as the target sequence, it is important to minimize competition for the probe between the target sequence and the counterprobe so that the counterprobe does not displace the probe from target sequence.

What is claimed is:

1. A synthetic, non-naturally occurring composition comprising the structure:

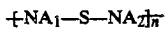

wherein $NA_1$ and $NA_2$ are different noncomplementary nucleic acid sequences;

wherein —S— is a scissile linkage which is capable of being cleaved or disrupted without cleaving or disrupting the nucleic acid sequences of $NA_1$ or $NA_2$ or of a target nucleic acid sequence capable of hybridizing to the $NA_1$ and $NA_2$ sequences, or to the $NA_1$ and $NA_2$ sequences and the scissile linkage of said composition, wherein if the scissile linkage is a nucleic acid sequence it is RNA when both $NA_1$ and $NA_2$ are DNA sequences, or the scissile linkage is DNA when both $NA_1$ and $NA_2$ are RNA sequences; and wherein n is an integer from 1 to 4.

2. The composition of claim 1, wherein the dashed lines represent chemical bonds.

3. The composition of claim 2, wherein the chemical bonds are covalent bonds.

4. The composition of claim 1, wherein the scissile linkage is selected from the group consisting of RNA sequences, DNA sequences, amino acid sequences, abasic nucleic acid sequences or carbohydrate polymers.

5. The composition of claim 1, wherein the scissile linkage is a nucleic acid sequence.

6. The composition of claim 1 immobilized on a solid support.

7. The composition of claim 1, wherein $NA_1$ and $NA_2$ are DNA sequences.

8. The composition of claim 1, wherein $NA_1$ and $NA_2$ are RNA sequences.

9. The composition of claim 1, wherein when the scissile linkage is other than a nucleic acid sequence $NA_1$ is either an RNA or DNA sequence and $NA_2$ is either an RNA or DNA sequence.

10. The molecule of claim 1, wherein $NA_1$ or $NA_2$ comprises a sequence which is not a naturally occurring nucleic acid sequence.

11. The composition of claim 1, wherein $NA_1$ or $NA_2$ is a naturally occurring nucleic acid sequence.

12. The composition of claim 1, wherein in each $-NA_1-S-NA_2$] a marker is attached to one of $NA_1$ or $NA_2$.

13. The composition of claim 12 immobilized on a solid support.

14. The composition of claim 12, wherein the marker is a radioisotope, a radiolabelled molecule, a fluorescent molecule, biotin, an enzyme, or a ligand.

15. The composition of claim 1, wherein $NA_1$ and $NA_2$ each comprise between 8 nucleotides and 10,000 nucleotides.

16. The composition of claim 1, wherein n is greater than 1 and each $[NA_1-S-NA_2]$ unit is the same.

17. The composition of claim 1, wherein n is greater than 1 and each $[NA_1-S-NA_2]$ unit is different.

18. A synthetic, non-naturally occurring composition comprising the structure:

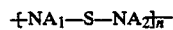

wherein $NA_1$ and $NA_2$ are nucleic acid sequences;

wherein —S— is a scissile linkage which is capable of being cleaved or disrupted without cleaving or disrupting the nucleic acid sequences of $NA_1$ or $NA_2$ or of a target nucleic acid sequence capable of hybridizing to the $NA_1$ and $NA_2$ sequences, or to the $NA_1$ and $NA_2$ sequences and the scissile linkage of said composition, wherein if the scissile linkage is a nucleic acid sequence it is RNA when both $NA_1$ and $NA_2$ are DNA sequences, or the scissile linkage is DNA when both $NA_1$ and $NA_2$ are RNA sequences; and wherein n is an integer from 2 to 4.

19. The composition of claim 18, wherein a marker is attached to one of $NA_1$ or $NA_2$.

20. The composition of claim 18 immobilized on a solid support.

21. A composition comprising the structure:

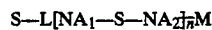

wherein $NA_1$ and $NA_2$ are nucleic acid sequences;

wherein —S— is a scissile linkage which is capable of being cleaved or disrupted without cleaving or disrupting the nucleic acid sequences of $NA_1$ or $NA_2$ or of a target nucleic acid sequence capable of hybridizing to the $NA_1$ and $NA_2$ sequences, or to the $NA_1$ and $NA_2$ sequences and the scissile linkage of said composition, wherein if the scissile linkage is a nucleic acid sequence it is RNA when both $NA_1$ and $NA_2$ are DNA sequences, or the scissile linkage is DNA when both $NA_1$ and $NA_2$ are RNA sequences;

wherein n is an integer from 1 to 4;

wherein the solid lines represent chemical bonds;

wherein X is a solid support;

wherein L is a chemical entity which links $NA_1$ to the solid support; and wherein M is a marker.

22. The composition of claim 21, wherein X is a silicaceous, cellulosic, or plastic material or controlled pore glass.

23. The composition of claim 21, wherein the chemical bonds are covalent bonds.

24. The composition of claim 21, wherein the chemical bonds are hydrogen or covalent bonds.

25. The composition of claim 21, wherein M is a radioisotope, a radiolabelled molecule, a fluorescent molecule, or a ligand.

26. The composition of claim 21, wherein the dashed lines represent chemical bonds.

27. The composition of claim 26, wherein the chemical bonds represented by the dashed lines are covalent bonds.

28. The composition of claim 21, wherein the scissile linkage is selected from the group consisting of RNA sequences, DNA sequences, amino acid sequences, abasic nucleotide sequences or carbohydrate polymers.

29. The composition of claim 21, wherein $NA_1$ and $NA_2$ each comprise between 8 nucleotides and 10,000 nucleotides.

30. The composition of claim 21, wherein n is greater than 1 and each $[NA_1-S-NA_2]$ unit is the same.

31. The composition of claim 21, wherein n is greater than 1 and each $[NA_1-S-NA_2]$ unit is different.

32. A composition comprising the structure:

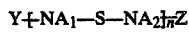

wherein $NA_1$ and $NA_2$ are nucleic acid sequences;
wherein —S— is a scissile linkage which is capable of being cleaved or disrupted without cleaving or disrupting the nucleic acid sequences of $NA_1$ or $NA_2$ or of a target nucleic acid sequence capable of hybridizing to the $NA_1$ and $NA_2$ sequences, or to the $NA_1$ and $NA_2$ sequences and the scissile linkage of said composition, wherein if the scissile linkage is a nucleic acid sequence it is RNA when both $NA_1$ and $NA_2$ are DNA sequences, or the scissile linkage is DNA when both $NA_1$ and $NA_2$ are RNA sequences;
wherein the solid lines represent chemical bonds;
wherein n is an integer from 1 to 4;
wherein Y is absent or is a chemical entity which confers an identifying characteristic; and
wherein Z is absent or is a chemical entity which confers a different identifying characteristic.

33. The composition of claim 32, wherein the chemical bonds are covalent bonds.

34. The composition of claim 32, wherein the identifying characteristic of Y is hydrophobicity or hydrophilicity and the identifying characteristic of Z is hydrophilicity or hydrophobicity.

35. The composition of claim 32, wherein when one of Y or Z is absent, the other is hydrophobic.

36. The composition of claim 32, wherein the dashed lines represent chemical bonds.

37. The composition of claim 36, wherein the chemical bonds represented by dashed lines are covalent bonds.

38. The composition of claim 32, wherein the scissile linkage is selected from the group consisting of RNA sequences, DNA sequences, amino acid sequences, abasic nucleotide sequences or carbohydrate polymers.

39. The composition of claim 32, wherein one of Y or Z is a marker and the other is hydrophobic.

40. The composition of claim 32, wherein a marker is attached to one of $NA_1$ or $NA_2$.

41. The compositiion of claim 32, wherein $NA_1$ and $NA_2$ are DNA sequences.

42. The composition of claim 32, wherein $NA_1$ and $NA_2$ are RNA sequences.

43. The composition of claim 32, wherein when the scissile linkage is other than a nucleic acid sequence $NA_1$ is either an RNA or DNA sequence and $NA_2$ is either an RNA or DNA sequence.

44. The composition of claim 32, wherein $NA_1$ and $NA_2$ comprises a sequence which is not a naturally occurring nucleic acid sequence.

45. The composition of claim 32, wherein $NA_1$ or $NA_2$ is a naturally occurring nucleic acid sequence.

46. A method of detecting in a sample the presence of a target nucleic acid sequence of interest comprising:
(a) contacting the sample with a composition of claim 12 which comprises a nucleic acid sequence substantially complementary to the target nucleic acid sequence of interest, under hybridizing conditions to form a hybridized complex;
(b) immobilizing said complex on a solid support;
(c) treating the immobilized complex so as to cleave the scissile linkage;
(d) separately recovering the immobilized complex; and
(e) detecting the presence of the marker on the immobilized complex and thereby the target nucleic acid sequence of interest.

47. A method of detecting in a sample the presence of a target nucleic acid sequence of interest comprising:
(a) contacting the sample with a composition of claim 21 which comprises a nucleic acid sequence substantially complementary to the target nucleic acid sequence of interest, under hybridizing conditions to form a hybridized complex;
(b) treating said complex so as to cleave the scissile linkage;
(c) separately recovering the immobilized complex; and
(d) detecting the presence of the marker on the immobilized complex and thereby the target nucleic acid sequence of interest.

48. A method of detecting in a sample a target nucleic acid sequence of interest comprising:
(a) contacting under hybridizing conditions the sample with an aqueous solution comprising a composition of claim 40 which comprises a nucleic acid sequence complementary to the target nucleic acid sequence of interest to form a hybridized complex, wherein Y is a hydrophobic entity and Z is a hydrophilic entity;
(b) mixing the resulting solution with a nonpolar solvent to form a biphasic solution in which the complex is present at the phase interface of the biphasic solution, Y being oriented in one phase and Z being oriented in the other phase;
(c) treating the complex so as to cleave the scissile linkage;
(d) recovering the complex so treated; and
(e) detecting the presence of the marker and thereby detecting the target nucleic acid sequence of interest.

49. A diagnostic method for detecting the presence of a foreign pathogen in a sample which comprises detecting a nucleic acid sequence characteristic of the pathogen using the method of any of claims 46-48.

50. A method for quantitatively determining in a sample the amount of a target nucleic acid sequence of interest comprising:
(a) contacting the sample with a predetermined amount of a composition of claim 12, which comprises a nucleic acid sequence substantially complementary to the target nucleic acid sequence of interest, under hybridizing conditions to form a hybridized complex;

(b) immobilizing said complex on a solid support;

(c) treating the immobilized complex so as to cleave the scissile linkage;

(d) separately recovering the immobilized complex; and (e) quantitatively determining the amount of marker present on the immobilized complex and thereby the amount of target nucleic acid sequence of interest.

51. A method for quantitatively determining in a sample the amount of a target nucleic acid sequence of interest comprising:

(a) contacting the sample with a predetermined amount of a composition of claim 21, which comprises a nucleic acid sequence substantially complementary to the target nucleic acid sequence of interest, under hybridizing conditions to form a hybridized complex;

(b) treating the immobilized complex so as to cleave the scissile linkage;

(c) separately recovering the immobilized complex; and (d) quantitatively determining the amount of marker present on the immobilized complex and thereby the amount of target nucleic acid sequence of interest.

52. A method for quantitatively determining in a sample the amount of a target nucleic acid sequence of interest comprising:

(a) contacting under hybridizing conditions the sample with an aqueous solution comprising a composition of claim 40 which comprises a nulceic acid sequence complementary to the target nucleic acid sequence of interest to form a hybridized complex, wherein Y is a hydrophobic entity and Z is a hydrophilic entity;

(b) mixing the resulting solution with a nonpolar solvent to form a biphasic solution in which the complex is present at the phase interface of the biphasic solution, Y being oriented in one phase and Z being oriented in the other phase;

(c) treating the complex so as to cleave the scissile linkage;

(d) recovering the complex so treated; and (e) quantitatively determining the amount of a marker and thereby the target nucleic acid sequence of interest.

53. A diagnostic method for measuring the amount of a foreign pathogen in a sample which comprises detecting a nucleic acid of the pathogen using the method of any of claims 50–52.

* * * * *